(12) United States Patent  
Benson et al.

(10) Patent No.: US 8,317,023 B2  
(45) Date of Patent: Nov. 27, 2012

(54) PACKAGE FOR CONSUMER PRODUCT

(75) Inventors: William Mercer Benson, Harrison, OH (US); Peter Michael Searles, Mason, OH (US); Linda Marie Bumpass, Crestview Hills, KY (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 13/169,908

(22) Filed: Jun. 27, 2011

(65) Prior Publication Data

US 2011/0253578 A1  Oct. 20, 2011

Related U.S. Application Data

(62) Division of application No. 11/800,931, filed on May 8, 2007, now Pat. No. 8,136,664.

(51) Int. Cl.  
*B65D 85/16* (2006.01)

(52) U.S. Cl. ............... 206/494; 206/440; 206/459.5

(58) Field of Classification Search ......... 206/438, 206/440, 459.5, 494, 812; 604/385.02; 40/310–312  
See application file for complete search history.

(56) References Cited

U.S. PATENT DOCUMENTS

| | | | |
|---|---|---|---|
| 4,214,028 A | 7/1980 | Shortway et al. | |
| 4,217,385 A | 8/1980 | Shortway et al. | |
| 4,248,922 A | 2/1981 | Shortway et al. | |
| 4,491,616 A * | 1/1985 | Schmidle et al. | 428/158 |
| 4,939,992 A | 7/1990 | Bird | |
| 6,601,705 B2 * | 8/2003 | Molina et al. | 206/494 |
| 6,949,290 B2 | 9/2005 | Schaeffeler et al. | |
| 7,185,453 B2 * | 3/2007 | Spear et al. | 40/638 |
| 7,185,761 B2 | 3/2007 | Molina et al. | |
| 2003/0120241 A1 | 6/2003 | Sorebo et al. | |
| 2005/0209539 A1 * | 9/2005 | Lev et al. | 601/22 |
| 2006/0025739 A1 * | 2/2006 | DiPalma et al. | 604/385.02 |
| 2006/0138008 A1 | 6/2006 | Simone et al. | |
| 2007/0032768 A1 | 2/2007 | Cohen et al. | |
| 2007/0142811 A1 * | 6/2007 | Lais | 604/385.02 |
| 2008/0145620 A1 | 6/2008 | Sahlberg et al. | |

FOREIGN PATENT DOCUMENTS

| | | |
|---|---|---|
| WO | WO 2005/108114 A2 | 11/2005 |
| WO | WO 2007/088274 A2 | 8/2007 |
| WO | WO 2007/132434 A | 11/2007 |

OTHER PUBLICATIONS

PCT Search Report dated Aug. 9, 2008, PCT/IB2008/051836 (6 pages).  
U.S. Appl. No. 11/800,931, filed May 8, 2007, Office Action dated Dec. 14, 2009, Restriction Requirement.

(Continued)

*Primary Examiner* — Luan K Bui  
(74) *Attorney, Agent, or Firm* — Megan C. Hymore; Roddy M. Bullock

(57) ABSTRACT

A package comprising an externally visible face. The externally visible face comprises embossed indicia, said indicia being in the shape of a droplet and having disposed thereon a relatively glossy or shiny coating. The externally visible face comprises an additional coating surrounding the indicia, the additional coating being relatively non-glossy. Or, the externally visible face comprises embossed indicia, the indicia having disposed thereon a relatively non-glossy coating. The externally visible face comprises an additional coating surrounding the indicia, the additional coating being relatively glossy or shiny.

20 Claims, 5 Drawing Sheets

OTHER PUBLICATIONS

U.S. Appl. No. 11/800,931, filed May 8, 2007, Office Action dated Mar. 11, 2010.
U.S. Appl. No. 11/800,931, filed May 8, 2007, Office Action dated Oct. 15, 2010.
U.S. Appl. No. 11/800,931, filed May 8, 2007, Office Action dated Mar. 25, 2011.
U.S. Appl. No. 11/800,931, filed May 8, 2007, Office Action dated Jul. 19, 2011.

* cited by examiner

US 8,317,023 B2

PACKAGE FOR CONSUMER PRODUCT

CROSS REFERENCES TO RELATED APPLICATIONS

This application is a divisional of U.S. application Ser. No. 11/800,931, filed May 8, 2007, now U.S. Pat. No. 8,136,664.

FIELD OF THE INVENTION

This invention relates to the field of packaging for consumer products.

BACKGROUND OF THE INVENTION

Consumer products are marketed to consumers, generally at retail outlets. Consumer products are often marketed at the point of sale in protective packaging, such as boxes, containers, bags, blister packs, cartons, and the like. In addition to being protective, packaging for consumer products is attractive and eye-catching so that consumers might stop and consider purchasing the packaged products. Manufacturers also desire to make product packaging informative so that consumers can determine accurate information about a product from looking at and/or handling the packaging.

There is a continuing need for packaging for consumer products that is eye-catching to consumers at the point of sale.

Additionally, there is a need for packaging that not only provides a pleasant appearance that causes consumers to stop and look, but which also has structural features that help educate a consumer as to the product inside the package.

Further, there is a need for packaging that has consumer-desirable features such as soft, smooth tactile impression, but which is durable enough for shipping and handling.

SUMMARY OF THE INVENTION

A package comprising an externally visible face is disclosed. The externally visible face comprises indicia, the indicia having disposed thereon a relatively glossy or shiny coating. The externally visible face is embossed in a portion corresponding to the indicia. The externally visible face comprises an additional coating surrounding the indicia, the additional coating being relatively non-glossy. The indicia is non-alphanumeric.

DETAILED DESCRIPTION OF THE INVENTION

DETAILED DESCRIPTION OF THE INVENTION

Consumer products are manufactured articles intended to be sold at retail stores to consumers, who then use such products for their intended use. Examples of consumer products include electronic products such as televisions and computers; automotive products such as after-market parts and accessories; car care products such as washes and waxes; home care products such as floor cleaners and air fresheners; oral care products such as toothpaste and mouthwash; laundry products such as detergents and fabric softeners; clothing, jewelry, and beauty care products such as hair care and body care creams, gels, and conditioners, and skin care products such as lotions and razors. One class of consumer products is disposable absorbent articles, which includes disposable diapers, training pants, incontinence pads and pants, sanitary napkins, tampons, pantiliners, wipes, wet wipes, bandages and pessaries. Most disposable absorbent articles are intended to be disposed of after a single use.

The present invention is useful for packaging materials that can be formed into permanent three-dimensional forms that can provide a tactile impression to a user. In general, packaging materials useful for the present invention include relatively stiff materials such as paper, paperboard, cardboard, and laminates of paper or cardboard. Packaging materials can also include thermoplastic, moldable materials, and laminates of paper and thermoplastic films. In general, three-dimensionality can be provided by molding, or by permanent deformation, such as by embossing, debossing, folding, punching, and the like. In one embodiment, the present invention can be a box made from a stamped, printed blank of paper, cardboard, or laminates thereof, as is well known in the art.

The invention is described below in relation to one embodiment of the present invention that is a package for containing disposable absorbent products. Disposable absorbent products can be individually wrapped and sealed in pouches, packets, or other outer wrapping and packaged for retail sale in the package of the present invention. For example, sanitary napkins can be folded, wrapped in an outer film wrapper, and stacked in package for sale to a consumer at a retail outlet. Likewise, wet wipes can be packaged individually in packets and stacked in a package for sale to consumers at a retail outlet. While the invention is described with respect to disposable absorbent products, the invention can be applied to other consumer products as desired.

Figure 1:
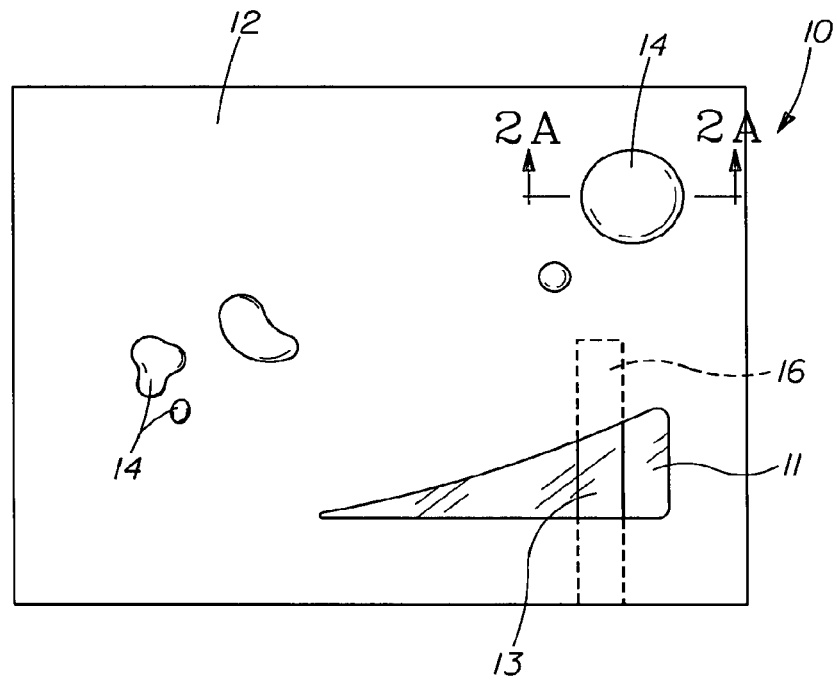
FIG. 1 is a view of one face of a package of the present invention.

FIG. 1 shows the front face of a package 10 of the present invention. Package 10 can be a box, and can be made of any materials known to be useful for packaging, and which can be processed to have permanent three-dimensional deformations. Package 10 can be made of paper, cardboard or laminates of packaging materials. Package 10 can be made of polymer film, film/paper laminate, or partially film and partially paper. Package 10 can be any suitable shape or size, and can be a six-sided box having four sides or faces, a top and a bottom. FIG. 1 shows one face 12 of a six-sided box, the face shown having four edges generally in the shape of a square, the edges being at the corners of a three-dimensional, parallel-piped-shaped package 10.

Externally visible face 12 of package 10 has printed thereon indicia 14 relevant to the product 16 packaged within package 10. In the embodiment shown in FIG. 1, the product 16 can be a disposable absorbent product, and specifically can be a wet wipe. Because product 16 can be a wet wipe, indicia 14 can be in the shape of droplets, such as water droplets, providing the impression that package 10 is wet.

At least one of the indicia 14 can be enhanced to provide visible and/or tactile impression to a consumer at the point of sale. For example, indicia 14 can be printed in vibrant colors, contrasting colors, or in a manner so at to provide an illusion of depth, shape, or consistency. For example, indicia 14 of package 10, being in the shape of water droplets on a surface, can be printed with appropriate shading, shadow, and color so as to appear three-dimensional when printed on a generally flat surface.

Figure 2A:
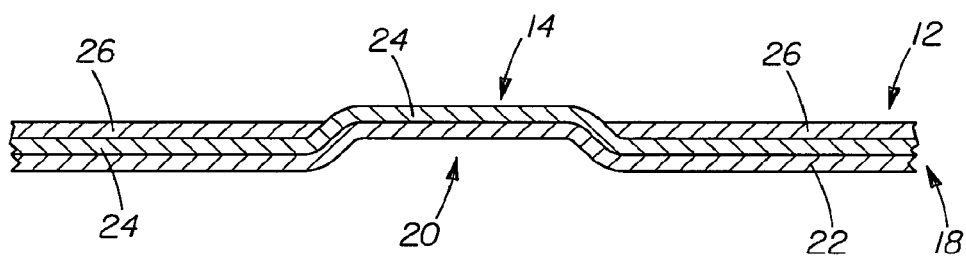
FIGS. 2A and 2B are cross-sectional representations of the portion 2-2 of the package shown in FIG. 1.
Figure 2B:
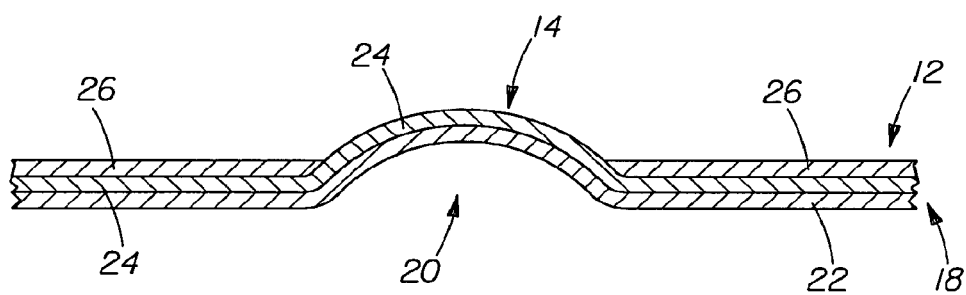

Because wetness is a feature that manufacturers of products such as wet wipes may want to communicate more strongly, the package 10 can be modified in the vicinity of indicia 14 in a manner that accentuates the indicia 14 and makes this feature stand out to a consumer viewing or holding the package 10. One way to accentuate indicia 14 is by embossing. As shown in FIGS. 2A and 2B, which are cross sections of one of indicia 14 in FIG. 1, embossing can result in a portion of packaging material 18 of face 12 being deformed from a generally flat configuration to an indented, pushed out, or otherwise formed embossed portion 20 that can correspond in size and shape to the size and shape of indicia 14.

By embossing visual indicia 14 the visual image is changed. In one embodiment, indicia 14 are non-alphanumeric, that is, they do not comprise numbers or letters of an alphabet. In one embodiment, indicia 14 can include in plan view at least one closed geometrical figure that can be a defined by a smooth regular boundary, such as a circle, or a smooth, irregular boundary, such as the figure of water droplets as illustrated in FIG. 1. For embossed water droplets, for example, embossed formed portion 20 can approximate the size and shape of water droplet image indicia 14 and can be registered with indicia 14 so as to provide for a three-dimensional visual-tactile image on package 10.

In one embodiment, indicia 14 can be further visually enhanced by application of an image-enhancing coating, ink, dye, or other visually-discernable material on at least a portion of the visible surface of an embossed image. For example, embossed portion 20 can have applied to the visible surface thereof a glossy coating, such that indicia 14, such as an image of a droplet of water, appears glossier than portions of package 10 surrounding indicia 14. In another embodiment, as shown in FIGS. 2A and 2B, packaging material 18 can comprise a paper, cardboard, paperboard, cartonboard, or other suitable packaging substrate 22. General images, such as colors, trademarks, product images and the like can be printed directly on to packaging substrate 22, as is known and commonly practiced in the product packaging field. In addition to general printed images, indicia 14 can be printed on packaging substrate 22. After indicia is printed, and an image-enhancing coating 24 can be applied, at least over and contiguous with a portion of indicia 14. Image-enhancing coating 24 can be applied directly over, and in complete registry with the boundary of indicia 14, or, as shown in FIGS. 2A and 2B, image-enhancing coating 24 can be applied over a substantial portion of, including all of, packaging substrate 22.

To make indicia 14 even more visually discernable to a consumer, the externally-visible portions of package 10 surrounding indicia 14 can have applied thereto, such as by printing, a contrasting color, finish, texture, or other visible attribute. For example, as shown in FIGS. 2A and 2B, packaging substrate 22 can be coated or printed with a contrasting coating 26. Contrasting coating 26 can be a matte finish, for example, if image-enhancing coating 24 makes a glossy finish. In one embodiment, indicia 14 can include reticulated coatings that can be made three dimensional by suitable exposure to UV or E-beam radiation treatments.

By enhancing indicia 14 with image-enhancing coating(s) 24 and also rendering portions of packaging 10 surrounding indicia with contrasting coating(s) 26, the visible representation of indicia 14 can be significantly improved. For example, in the example shown in FIG. 1, indicia 14 in the form of images of water droplets can be enhanced with a relatively glossy finish that renders the water droplets shiny, and the indicia can be further enhanced by rendering the portion of packaging 10 around the water droplet images to be relatively less shiny, including dull or matte finish. In one embodiment the indicia of the present invention can make the package look like it is wet, the indicia appearing very close to actual drops of water on the exterior surface of packaging 10. Although foil in the form of foil embossing and foil stamping as is known in the art is contemplated and can be incorporated in some embodiments of the invention, in other embodiments, the indicia is foil-free.

Figure 3:
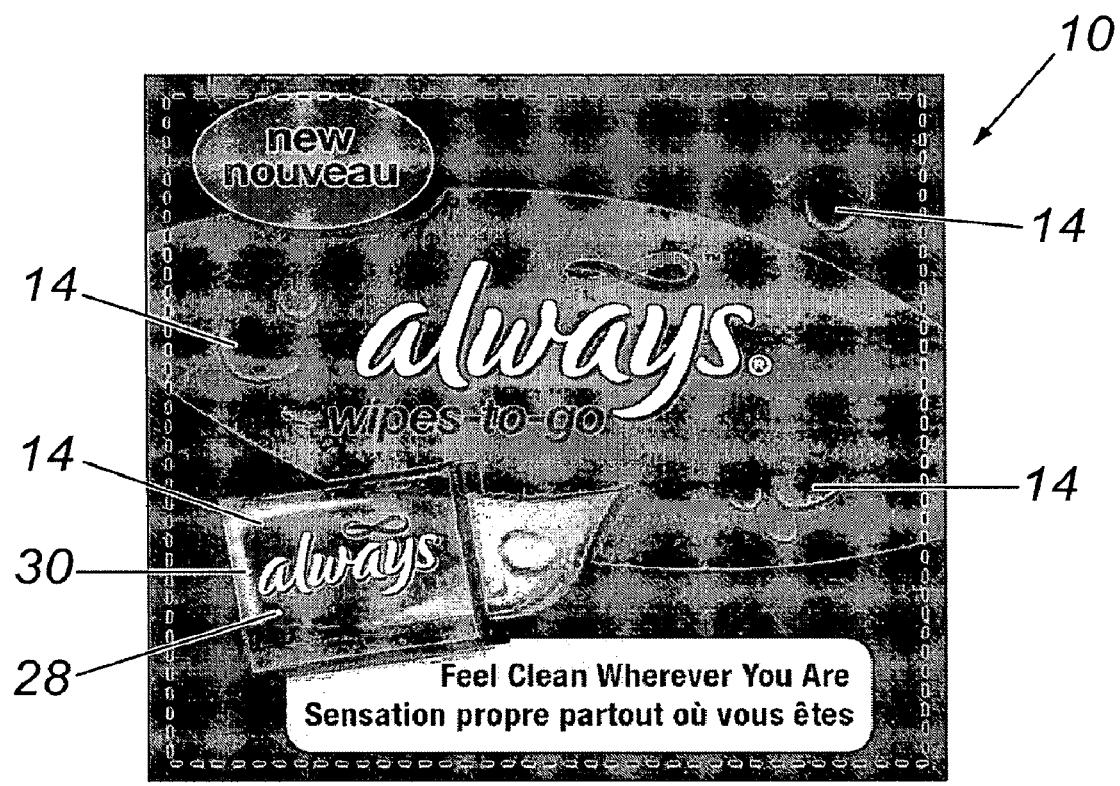
FIG. 3 is a view of one face of a package of the present invention.

FIG. 3 shows an embodiment of one face of a package 10 in which is contained wet wipes. In addition to general printed information such as the brand name ALWAYS®, a trademarked logo, an image of the product inside, and other informational printing, there is visible indicia 14. The package can have embossed portions 20 that can correspond in size and shape to the size and shape of each indicia 14, which as shown are images of water droplets on a surface, intended to appear as water droplets on face 12 of package 10. Additionally, each indicia 14 can be relatively glossy relative to portions of package 10 immediately surrounding each indicia 14. In one embodiment, indicia 14 can have a metallic surface. In another embodiment, the relative sheen or glossiness of the two portions can be varied or even reversed. That is, in one embodiment, the indicia 14 can include relatively matte finish, while the surrounding packaging material can be a relatively glossy finish. Although foil in the form of foil embossing and foil stamping as is known in the art is contemplated and can be incorporated in some embodiments of the invention, in other embodiments, the embossed portion is foil-free.

In one embodiment, indicia 14 can be an image of the packaged product, for example, product 13 as shown in FIG. 1. For example, in FIG. 2, indicia 14 can be the graphic representation of one wet wipe packet 28, the graphic representation shown in FIG. 3 with a portion of a wet wipe having thereon droplets of water. Wipe packet 28 can be raised relative to the surface of package 10, and can be an embossed portion 20 having a relatively glossy finish as described above. In such embodiments indicia 14 can be considered product indicia 30, that is, graphic representations showing product features to show a consumer what products and product features are inside the package 10. Although foil in the form of foil embossing and foil stamping as is known in the art is contemplated and can be incorporated in some embodiments of the invention, in other embodiments, the embossed portion 20 is foil-free.

Figure 4:
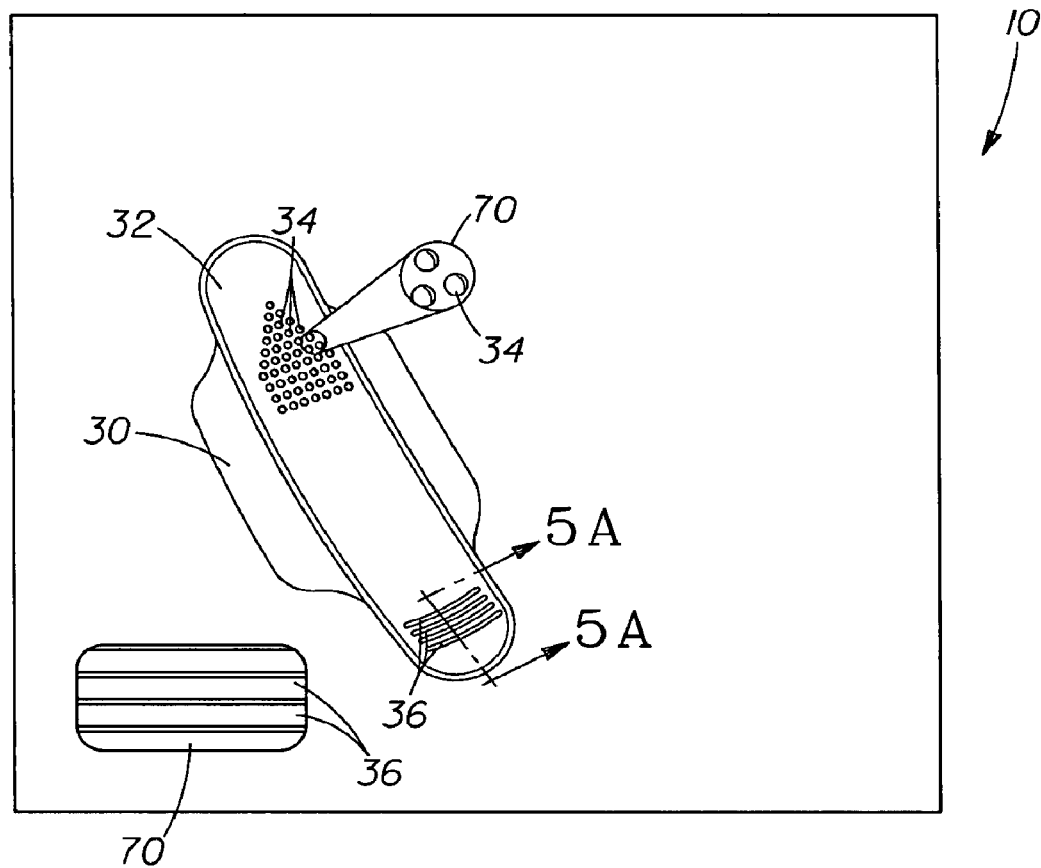
FIG. 4 is a view of one face of a package of the present invention.

FIG. 4 shows one face of a package 10, which can be the front face of a box package 10, having graphically represented thereon a product indicia 30 that is representative of a sanitary napkin 32 packaged inside package 10. In the illustrated embodiment, sanitary napkin 32 has a shape defining generally two ends and two sides having (in the illustrated embodiment) shaped wing flaps. In the illustrated embodiment, the part of the sanitary napkin intended to be worn toward the front when used is nearer the top of FIG. 4. Sanitary napkins are one form of absorbent articles, which can also include diapers, tampons, pantiliners, incontinence devices, bandages, and the like.

In one embodiment, the package 12 can have an externally visible face 12 having printed thereon an image of a having printed thereon an image of a product 13, such as an absorbent article, contained in the package 12. The image can include a two-dimensional visual representation of a three-dimensional feature on the product. The externally visible face can be embossed in a portion corresponding to the image of the absorbent article. The embossed portion can be three-dimensional deformed portions of the externally visible face, and the three-dimensional deformed portions can correspond to the two-dimensional graphical representation of the three-dimensional feature on the absorbent article.

The absorbent article, such as the sanitary napkin 32 shown can have various features that are visibly or tactilely evident to a user, and which the manufacturer would like to convey to a consumer at the point of sale. For example, the packaged sanitary napkin can have a textured surface, or can have apertures or holes in the absorbent core, or can have slits or slots in various portions, including in the absorbent core. In the illustrated embodiment, a sanitary napkin 32 is depicted on package 10, in which the sanitary napkin has holes in the absorbent core represented graphically as a plurality of dots or circles 34. Plurality of dots or circles 34 can be arranged in a pattern defining an overall shape, such as the generally pointed "shield" shape shown in FIG. 4. In the illustrated embodiment, sanitary napkin also has transverse slots in the absorbent core represented graphically as a plurality of generally elongated oval shapes 36.

In one embodiment of the present invention, the graphical representations of product features shown on package 10 are enhanced by shape-relevant embossing. That is, for dots or circles 34, package 10 can be embossed in a pattern of generally round embossments, and elongated oval shapes can be embossed in corresponding linear shapes. Embossed portions can be registered or partially registered with graphic indicia. In one embodiment, the shape of embossed portions (circular or elongated) need not correspond exactly or approximately to the graphic shape with which it is (or they are) registered. That is, circular-shaped embossed bumps could be registered with generally elongated oval shapes and still deliver significant benefit to the consumer.

Figure 5A:
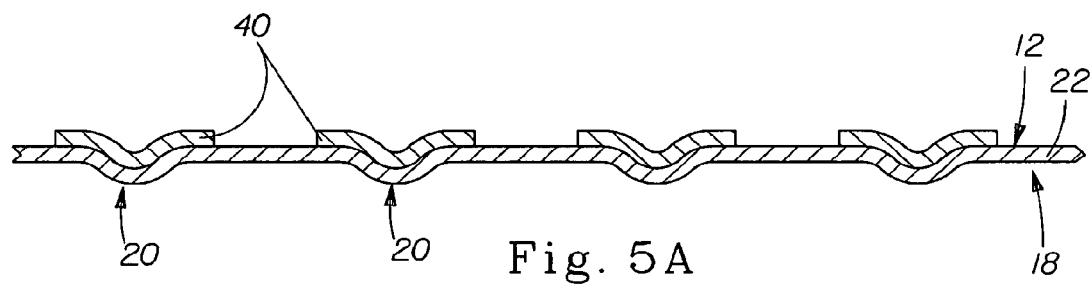
FIGS. 5A-5C are cross-sectional representations of the portion 5-5 of the package shown in FIG. 4.
Figure 5B:
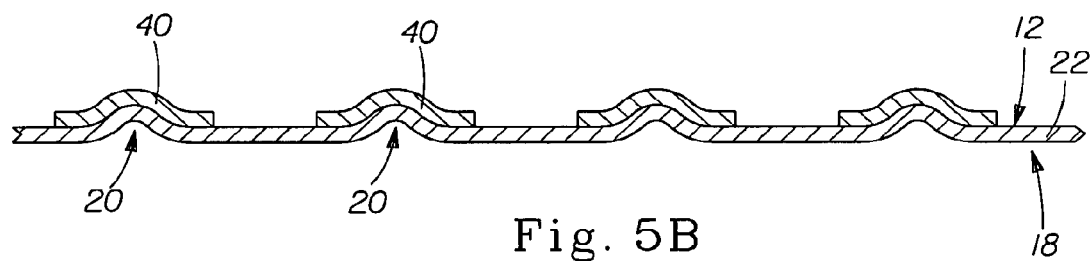
Figure 5C:
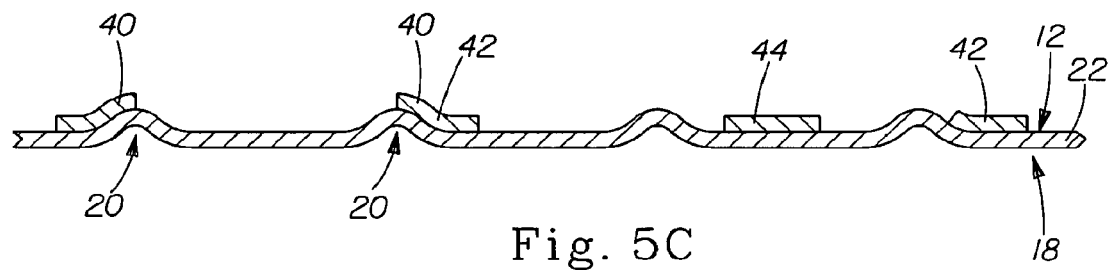

FIGS. 5A-5C show cross-section 5-5 from FIG. 4, which is a cross section of generally elongated embossed portions 20. In FIG. 5A, embossed portions 20 are embossed inwardly (i.e., debossed) with respect to the externally visible face 12. Product indicia 30 can be printed on by applying ink, dyes, or other pigments 40 in registration with embossed portions 22. In general, the printed portions 40 or the embossed portions 20 can be achieved in any order, or simultaneously. For example, in one embodiment, graphic images including product indicia 30 or indicia 14 can be printed on cartonboard, which can then be embossed with embossing tooling and registered with graphics as described herein. Embossed, registered graphic-printed cartonboard can then be die cut into package blanks by means known in the art. Die-cut blanks can be folded into the finished package 10 configuration by means known in the art, including by hand.

As shown in FIG. 5B, embossed portions 20 can extend outwardly with respect to the externally visible face 12, and printed portions 40 can be applied on the embossed portions.

As shown in FIG. 5C, it is not necessary that the printed portions 40 and embossed portions 20 be in precise registration. In certain embodiments, printed portion 40 can be in partial registration, as shown at 42 in FIG. 5C. In certain embodiments, printed portion 40 can be in close proximity but not in registration with embossed portion 20 as shown at 44 in FIG. 5C.

The depictions of cross-sections in FIGS. 5A-5C can also be applied to a cross-section through dots or circles 34, with the same variations and descriptions.

Figure 6:
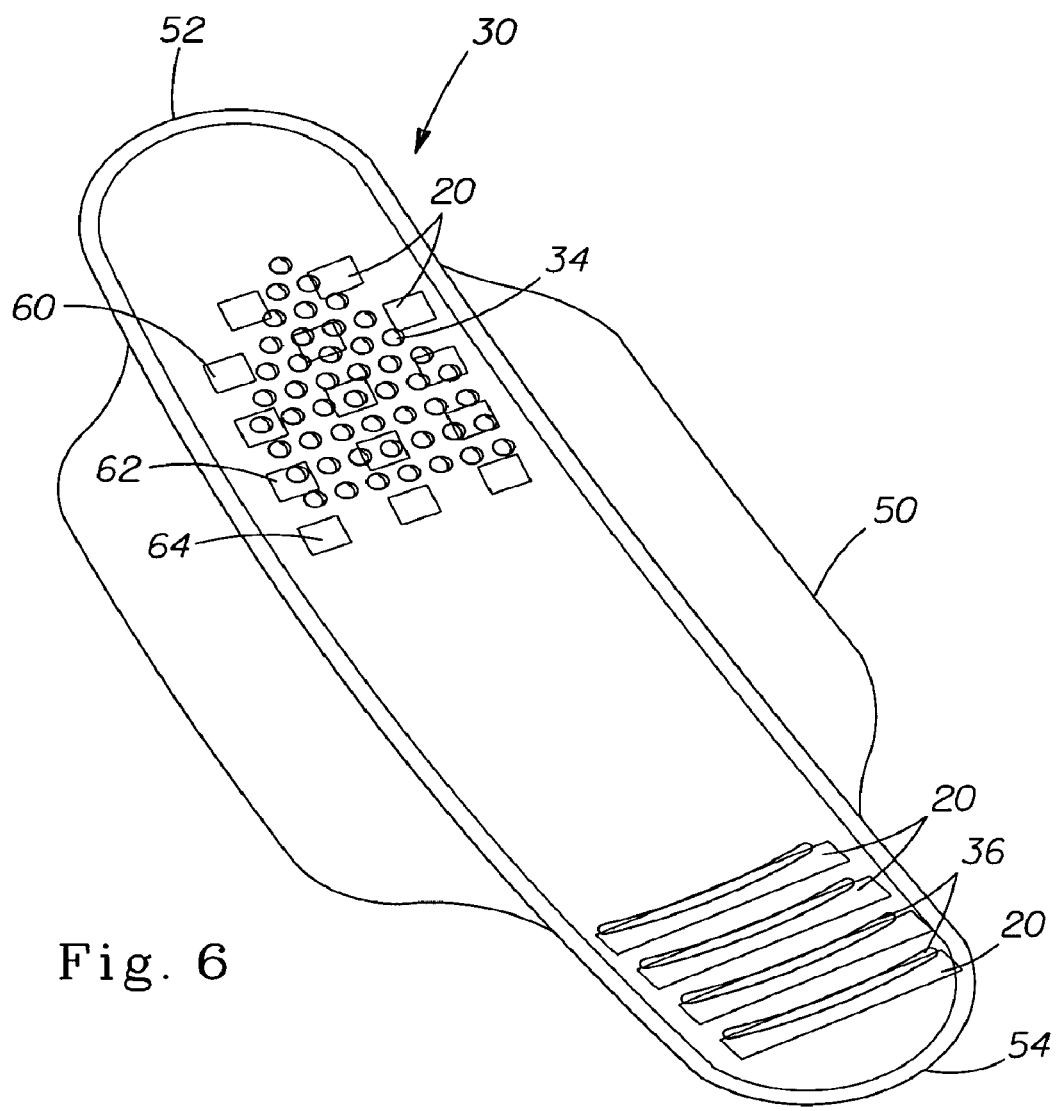
FIG. 6 is a schematic representation of a portion of the package of the present invention.

FIG. 6 is an enlarged detail of the product indicia 30 shown in FIG. 4. Product indicia 30 has a peripheral boundary 50 that is a closed geometrical shape that can entirely formed of smooth curved shapes. In the embodiment shown, product indicia 30 represents a sanitary napkin having a front 52, a back 54, an absorbent core having visually and tactilely perceivable physical features, such as holes and slots. Physical features such as holes and slots in the absorbent core of the packaged sanitary napkin are graphically represented in product indicia 30 as printed dots or circles 34 and printed elongated oval shapes 36, respectively.

Patterns of embossments 20 can be registered with, or approximately registered with patterns of printed graphical features. For example, as shown, a pattern of embossments 20 in the shape of squares or rounded squares can be registered with a corresponding pattern of dots or circles 34, and a pattern of generally elongated embossments 20 can be registered with a pattern of printed elongated oval shapes 36. In this manner, a person looking at or handling package 10 can see and/or feel a representation of product features, thereby better appreciating the products contained therein.

With reference again to FIG. 4, in one embodiment, further graphical images and corresponding embossing can aid a consumer in fully appreciating the product contained in a package 10. Enlarged representations 70 of visually and tactilely distinct product features can be made to provide the consumer inspecting the package with even more pronounced visual and tactile sensory detection. By enlarging the features graphically and with the same or enlarged corresponding embossed portions 20, the user can get a more pronounced impression of the desirable product features of the product contained in package 10.

Referring back to FIGS. 1 and 4, indicia 14 and/or product indicia 30 can be disposed on any face of a package 10, but can be most useful when disposed on an externally visible face 12, particularly a face intended to be outwardly oriented with respect to a retail shelf at the point of sale. Indicia 14 or product indicia 30 can be sized so as to cover from about 10%, 20%, 50% or about 90% of externally visible face 12. In general, indicia 14 and product indicia 30 can range from about 1 cm to about 10 cm in size, measured in a maximum dimension from one peripheral edge to another. In general, embossments 20 can have a maximum dimension of from about 1 mm to about 10 mm in size, measured in a maximum dimension.

Referring back to FIG. 1, package 10 can have other features such as a window 11. Window 11 can be an opening in face 12 of package 10 and can be a transparent window of polymer film. Window 11 can comprise clear, tinted, or translucent film, and can permit at least a portion of a packaged product 13 to be viewable from outside package 10. In general, window 11 and package 10 can be configured as disclosed in U.S. Pat. No. 7,185,761, issued Mar. 6, 2007 to Molina et al.

In one embodiment, package 10 can be a standard tuck flap carton constructed with a substrate 22 of 18 pt SBS board. Package 10 art can be produced utilizing 133 line screen digital Nudot flexographic plates provided by Phototype, printed on a central impression cylinder flexographic press.

Embossed portions 20 can have a high gloss overlacquer that can be applied in the following manner: Flexo Water base HIGH GLOSS Coating 150. Anilox at 9.8 BCM Siegwerk 10LD7209/25-DS. Package portions surrounding embossed portions 20 can be a matte, soft touch overlacquer applied in the following manner: Flexo Water base SOFT TOUCH Coating 250. Anilox at 7.8 BCM Siegwerk Part Number FUBM7U3BQ with added wax to increase the scuff resistance. Package material can then be cut per a die line on an inline flatbed die cutter, hand assembled, loaded with product, and hand packed into shipping containers.

Figure 7:
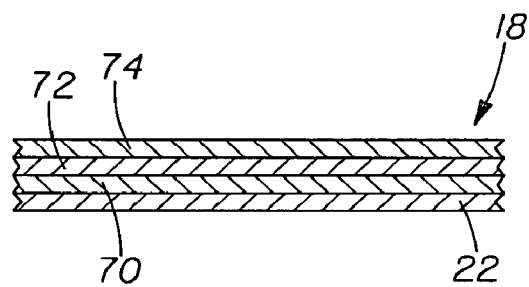
FIG. 7 is a cross-sectional representation of one embodiment of the present invention.

In one embodiment package 10 can comprise a burnish-resistant coating that provides for a relatively soft, smooth tactile impression. As shown in FIG. 7, at least a portion of packaging material 18 can be printed with a graphic layer 70. Graphic layer 70 can be any of known graphic such as colors, shapes, letters, numbers, logos, and the like, printed on by way of known printing processes. Packaging material can be further printed or coated with a so-called "soft touch" coating, such as the Siegwerk Part Number FUBM7U3BQ discussed above, or other coating comprising silica or silicone to provide for a soft or silky touch. To provide for good burnish resistance, and to otherwise protect the graphic layer 70 form being exposed and potentially rubbed off, a layer 72 of matte varnish, or other coating of high rub-off resistance can be applied between the graphic layer 70 and the soft touch layer 74. By using a matte varnish or overlaquer with silica, or other relatively hard, rub-off resistant coating between the soft touch coating and the graphic layer, the soft touch coating can comprise silicone and wax components using a relatively high silicone content. Burnish resistance refers to the propensity of the surface of the package to rub off, exposing layers underneath, or rubbing off ink from layers underneath. In one embodiment, the soft touch layer 74 and the matte varnish layer 72 can have a similar level of gloss, such that rub off of the soft touch layer 74 is not visibly evident due to the gloss difference between the soft touch layer 74 and the matte varnish layer 72.

The package can exhibit a relatively high coefficient of friction between the soft-feeling surface and a consumer's fingers, compared to ordinary print materials for consumer packaging. The soft-feeling surface finish provides packages with a feel that connotes to the user high quality, sophistication, and special attention to detail. In certain product categories, such as feminine hygiene articles, such connotations have never been present, and offer advantages to effectively marketing new, high end, expensive products. For a new but relatively expensive product offering, therefore, a manufacturer can produce a package having a soft, velvety touch wax finish that communicates richness and softness.

In all the embodiments disclosed, other methods for providing for glossiness are optionally possible. For example, in one embodiment, the package material 22 itself can have a glossiness due to a film lamination onto the underlying paper substrate. Glossy stickers can be added to portions of the package or packaging material to provide for a glossy portion of the package. Likewise, relatively less glossy surfaces and finishes can provide for a matte finish. In one embodiment a matte finish can be achieved by the use of a lamination of paperboard with a microembossed film or films coated with a matte finish coating.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package comprising an externally visible face, said externally visible face comprising embossed indicia; said indicia being in the shape of a droplet and having disposed thereon a relatively glossy or shiny coating; said externally visible face comprising an additional coating surrounding said indicia, said additional coating being relatively non-glossy; wherein said package comprises one or more absorbent articles; and wherein the package further comprises an image of an absorbent article contained within the package.

2. The package of claim 1, wherein said additional coating is a matte finish.

3. The package of claim 1, wherein said package additionally comprises a window.

4. The package of claim 1, wherein said indicia is bounded by a smooth regular boundary.

5. The package of claim 1, wherein said embossed indicia is in the shape of a water droplet and wherein said relatively glossy or shiny coating is in registration with said embossment.

6. The package of claim 1, wherein said embossed indicia is in the shape of a water droplet and wherein said relatively glossy or shiny coating is in partial registration with said embossment.

7. The package of claim 1, wherein said package comprises material selected from the group consisting of paper, cardboard, paperboard, cartonboard, and laminates thereof.

8. The package of claim 1, wherein said indicia appears three-dimensional.

9. The package of claim 1, wherein said indicia provide the impression that said externally visible face is wet.

10. The package of claim 1, wherein said package contains a plurality of absorbent articles.

11. A package comprising an externally visible face, said externally visible face comprising embossed indicia; said indicia being in the shape of a droplet and having disposed thereon a relatively non-glossy coating; said externally visible face comprising an additional coating surrounding said indicia, said additional coating being relatively glossy or shiny coating; wherein said package comprises one or more absorbent articles; and wherein the package further comprises an image of an absorbent article contained within the package.

12. The package of claim 11, wherein said relatively non-glossy coating is a matte finish.

13. The package of claim 11, wherein said package additionally comprises a window.

14. The package of claim 11, wherein said indicia is bounded by a smooth regular boundary.

15. The package of claim 11, wherein said embossed indicia is in the shape of a water droplet and wherein said relatively non-glossy coating is in registration with said embossment.

16. The package of claim 11, wherein said embossed indicia is in the shape of a water droplet and wherein said relatively non-glossy coating is in partial registration with said embossment.

17. The package of claim 11, wherein said package comprises material selected from the group consisting of paper, cardboard, paperboard, cartonboard, or laminates thereof.

18. The package of claim 11, wherein said indicia appears three-dimensional.

19. The package of claim 11, wherein said indicia provide the impression that said externally visible face is wet.

20. The package of claim 11, wherein said package contains a plurality of absorbent articles.

* * * * *